US00PP25027P3

(12) United States Plant Patent
Bourne

(10) Patent No.: US PP25,027 P3
(45) Date of Patent: Nov. 4, 2014

(54) ***DIANTHUS* PLANT NAMED 'WP11 GWE04'**

(50) Latin Name: *Dianthus×hybrida*
Varietal Denomination: WP11 GWE04

(71) Applicant: PlantHaven International, Inc., Santa Barbara, CA (US)

(72) Inventor: Carolyn Grace Bourne, Dawlish (GB)

(73) Assignee: Carolyn Grace Bourne (GB)

( * ) Notice: Subject to any disclaimer, the term of this patent is extended or adjusted under 35 U.S.C. 154(b) by 43 days.

(21) Appl. No.: 13/986,438

(22) Filed: May 2, 2013

(65) Prior Publication Data

US 2013/0305422 P1 Nov. 14, 2013

(30) Foreign Application Priority Data

May 10, 2012 (QZ) ..... PBR 20121030

(51) Int. Cl.
*A01H 5/00* (2006.01)

(52) U.S. Cl.
USPC ..... Plt./279

(58) Field of Classification Search
USPC ..... Plt./279, 274
See application file for complete search history.

*Primary Examiner* — Kent L Bell
(74) *Attorney, Agent, or Firm* — Barbara Campbell; Cochran Freund & Young LLC

(57) ABSTRACT

A new cultivar of *Dianthus* plant named 'WP11 GWE04' which is characterized by a compact mounding habit, gray-blue foliage, strongly fragrant white double flowers with ruffled petals and dentate margins, is disclosed.

2 Drawing Sheets

Genus and species: *Dianthus×hybrida.*

CROSS REFERENCE TO RELATED APPLICATIONS

This application claims the benefit of priority under 35 U.S.C. 119(f) of the earlier application for European Community Plant Variety Rights which was filed for the instant plant variety on May 10, 2012, Application Number 2012/1030.

BACKGROUND

The present invention relates to a new and distinct cultivar of hardy garden pink, that is grown for use as a flowering plant for pots and containers and for planting in the garden and landscape. The new cultivar is known botanically as *Dianthus×hybrida* and will be referred to hereinafter by the cultivar name 'WP11 GWE04'.

'WP11 GWE04' is a complex hybrid plant that is the product of a long term breeding program conducted by the inventor in a cultivated area of Houndspool, Dawlish, Devon, United Kingdom. The inventor selected 'WP11 GWE04' in 2004 for its double white flowers, ruffled petal edges, strong spicy clove-like fragrance and gray-blue foliage.

'WP11 GWE04' arose and was selected as a seedling which resulted from the controlled pollination of an existing selection of *Dianthus* from the inventor's breeding program, namely *Dianthus* code name 'ASH22' (unpatented and unreleased) as the female parent plant, by an existing selection of *Dianthus* from the inventor's breeding program, namely *Dianthus* code name 'Clujh' (unpatented and unreleased) as the male parent plant.

Asexual reproduction of 'WP11 GWE04' was first accomplished in 2004 in a cultivated area of Houndspool, United Kingdom. The method of asexual propagation used was vegetative cuttings. 'WP11 GWE04' is stable and reproduces true to type in successive generations of asexual propagation via vegetative cuttings.

COMPARISON BETWEEN PARENTAL AND COMMERCIAL VARIETIES

'WP11 GWE04' is distinguishable from the female parent as follows: Whereas the flower of 'WP11 GWE04' is double and white, the flower of 'ASH22' is semi-double and carmine in color. In addition, the foliage of the 'ASH22' is dark green in color, whereas the foliage of 'WP11 GWE04' is gray-blue in color.

'WP11 GWE04' is distinguishable from the male parent as follows: Whereas the flower of 'WP11 GWE04' is double and white, the flower of 'Chujh' is double and carmine in color.

The variety of *Dianthus* which is considered by the inventor to most closely resemble 'WP11 GWE04' is the double white flowered *Dianthus* 'Mrs. Sinkins' (unpatented). In comparison with 'WP11 GWE04', the habit of 'Mrs. Sinkins' has low plant vigor and exhibits an open rather than compact habit. In addition, 'Mrs. Sinkins' blooms predominantly in the spring only whereas 'WP11 GWE04' blooms almost continually from spring until fall.

SUMMARY

The following traits have been repeatedly observed and represent the characteristics of the new *Dianthus* cultivar 'WP11 GWE04'. These traits in combination distinguish this cultivar from all other commercial varieties known to the inventor. 'WP11 GWE04' has not been tested under all possible conditions and phenotypic differences may be observed with variations in environmental, climatic and cultural conditions, however, without any variance in genotype.

1. 'WP11 GWE04' exhibits a compact mounding habit.
2. 'WP11 GWE04' bears double white flowers.
3. The petals of 'WP11 GWE04' are gently ruffled with dentate margins
4. 'WP11 GWE04' blooms from Mid-April through October.
5. The flowers of 'WP11 GWE04' are strongly fragrant and spicy or clove-like.
6. 'WP11 GWE04' exhibits glaucous, gray-blue foliage.
7. At maturity, the height of the foliage mound of 'WP11 GWE04' is 35 cm, and the width is 25 cm.
8. 'WP11 GWE04' is perennial and is hardy at least to −15° C.
9. 'WP11 GWE04' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP11 GWE04' showing colors as true as it is reasonably possible to obtain in colored reproductions of this type. Colors in the photographs may differ from the color values cited in the detailed botanical description, which accurately describe the actual colors of the new variety 'WP11 GWE04'.

Figure 1:
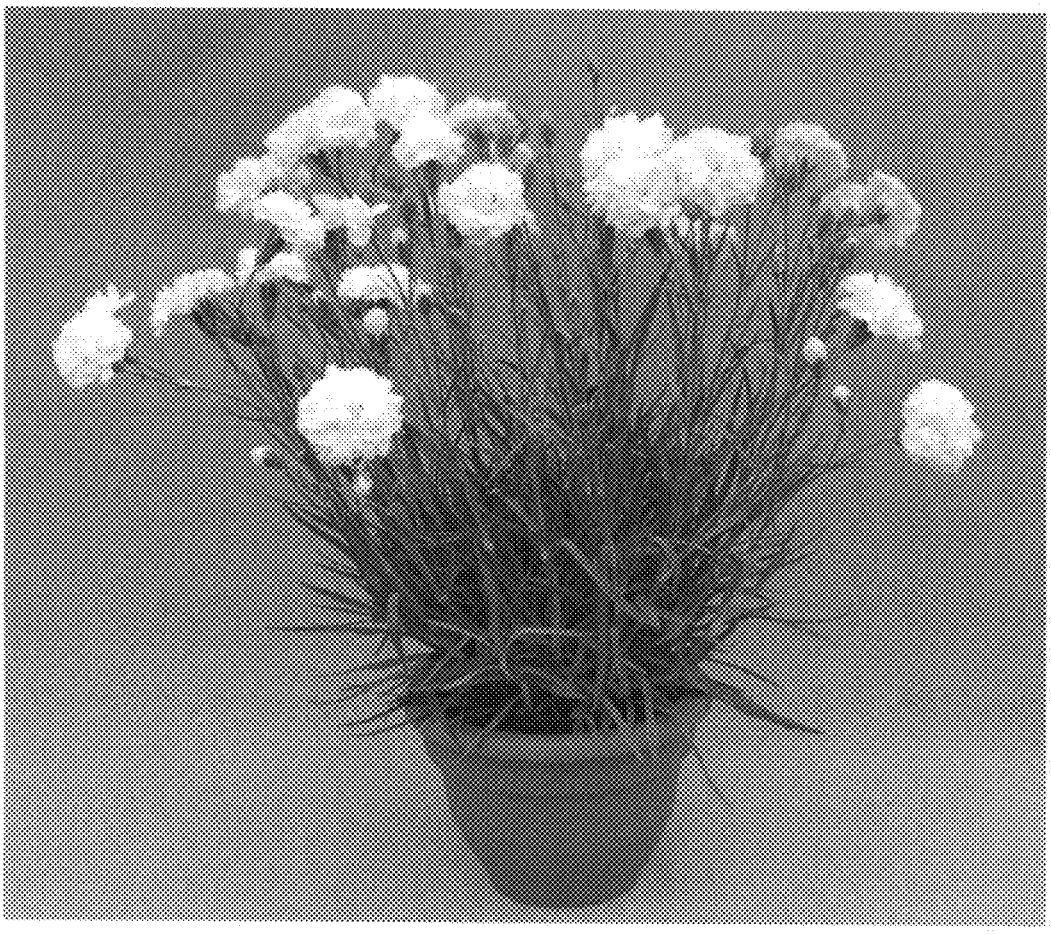
FIG. 1 depicts an entire flowering plant of 'WP11 GWE04'.
Figure 2:
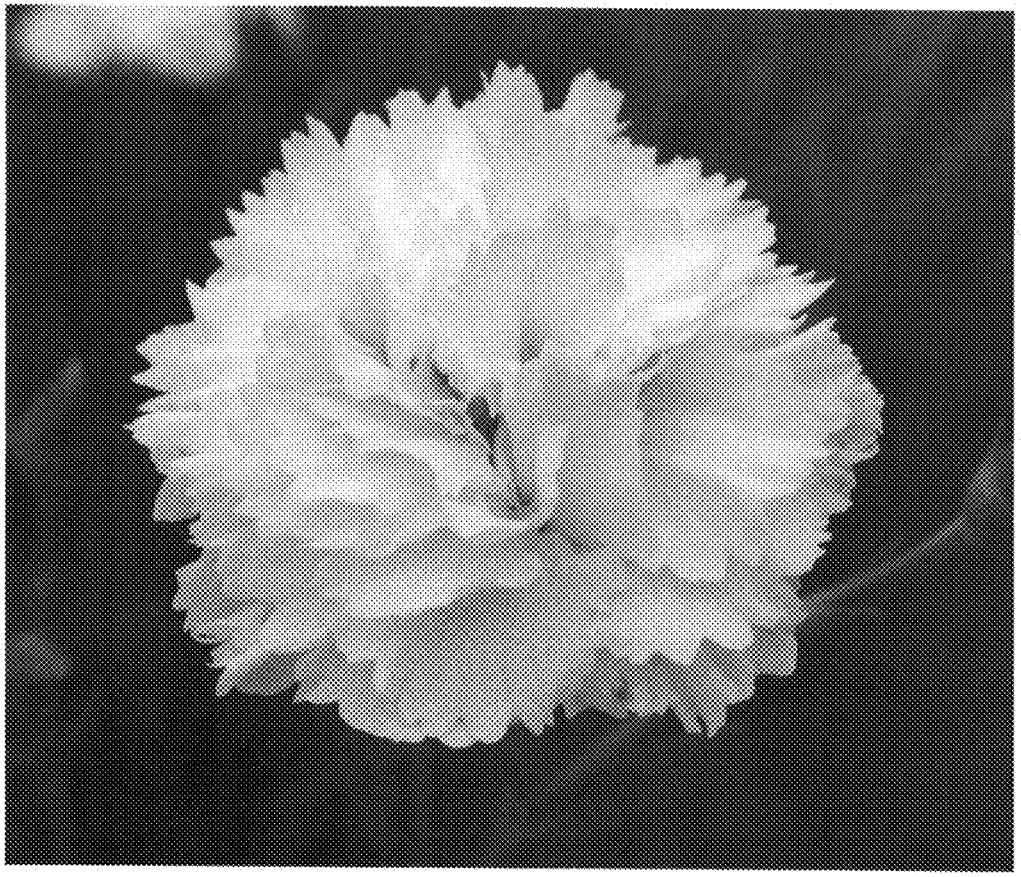
FIG. 2 depicts a close-up view of the flower of 'WP11 GWE04'.

All drawings were made from 9-month-old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'WP11 GWE04'. Data was collected from plants grown in 1.5 liter containers under an unheated glasshouse in Houndspool, United Kingdom. The color determinations are in accordance with the 2001 edition of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Classification:

*Botanical.*—*Dianthus*×*hybrida.*

*Denomination.*—'WP11 GWE04'.

*Common name.*—*Dianthus*, garden pink.

*Commercial classification.*—Hardy perennial herb.

Parentage: 'WP11 GWE04' is a hybrid plant that resulted from the cross pollination of two *Dianthus* breeding varieties.

*Female parent plant.*—*Dianthus* 'ASH22' plant (unpatented).

*Male parent plant.*—*Dianthus* 'Clujh' plant (unpatented).

Plant description:

*Use.*—Ornamental plant for pots and containers, cut flowers, bouquets.

*Bloom period.*—Mid April to October.

*Plant habit.*—Compact mounding habit.

*Plant height.*—35.0 cm in overall height, including flower canopy.

*Plant width.*—25.0 cm in width.

*Plant hardiness.*—Hardy to minus 15° Centigrade.

*Type.*—Perennial.

*Root system.*—Fibrous.

*Propagation.*—Propagation is accomplished using vegetative cuttings.

*Cultural requirements.*—Plant in full sun, well-drained and moderately fertile soil and keep well-fertilized and watered.

*Diseases and pests.*—Susceptible to known *Dianthus* pests and disease but no other susceptibilities to pests or disease are known.

*Time required to produce a rooted cutting.*—5 weeks are needed to produce a rooted cutting.

*Temperature recommended for cuttings to produce roots.*—The air temperature needed is a minimum of 15° Centigrade and base heat of 21° Centigrade.

*Crop time.*—3 to 6 months is needed to produce a finished 1.5-liter container size from a well-rooted cutting.

Foliage:

*Shoots* (*cutting*).—Shape: Cylindrical. Dimensions: 12.0 cm in length and 0.5 cm in diameter. Surface texture: Glabrous and glaucous. Color: RHS 145C (base of the cutting, then its leaf color). Branching: Numerous shoots from the axils of the lower leaves.

*Leaf.*—Type: Evergreen. Dimensions: 9.0 cm in length and 5.0 mm in width. Color (adaxial and abaxial surfaces): Ranges between RHS 189A to RHS 189B. Shape: Linear, straight. Division: Simple. Apex: Acute. Base: Decurrent. Venation: Not prominent. Margins: Entire. Attachment: Sheathing. Arrangement: Opposite and spiraling up stem. Surfaces (adaxial and abaxial): Glaucous. Stipules: Absent.

Flower stem (peduncle):

*Shape.*—Cylindrical.

*Dimensions.*—Approximately 11.0 cm in length (measured from the base of the calyx to lowest internode), 2.0 mm in width.

*Surface texture and appearance.*—Glabrous, waxy.

*Node.*—Swollen, 6.0 mm in diameter and 3.0 mm in length.

*Strength.*—Erect.

*Color.*—RHS N189C.

Flowers:

*Inflorescence type.*—Cymose.

*Shape.*—Salviform and symmetrical.

*Number.*—4 to 6 buds per stem.

*Dimensions* (*including calyx*).—40.0 mm in length and 50.0 mm in diameter.

*Shape.*—Circular.

*Lastingness.*—10 to 20 days at 20° Celsius on the plant; 8 to 10 days off the plant.

*Fragrance.*—Strong, spicy and clove-like.

*Flowering period.*—Mid-April to October.

*Bud.*—Shape: Obovate (when cracking color). Color: Ranges between RHS N138A at apex and RHS 144B at base. Anthocyanin: Absent. Dimensions: 22.0 mm to 25.0 mm in length and 11.0 mm in width (described when just cracking color).

*Corolla.*—Profile: Convex for the upper part and concave for the lower part. Petal arrangement: Persistent, apopetalous, overlapping. Margin: Crenate-dentate.

Indentations: 1.0 mm to 3.0 mm deep. Texture: Soft. Type: Double. Number of petals: 30 to 35 true petals plus 10 to 15 staminode petaloids. Dimensions: 43.0 mm in length, 20.0 mm in width. Petal shape: Obdeltoid. Petal surface: Glabrous, undulating. Petal apex: Fan shaped. Petal base: Strap shaped, tapering towards base. Color pattern: White throughout except for green hue at the base of the petal when very young. Petal color (both surfaces): Ground main color of blade: White (whiter than RHS NN155). Color of middle of strap: Ranges between RHS 145C and RHS 145D. Color of base of strap: RHS 149D when very young, becoming RHS 145D.

*Calyx*.—Calyx dimensions: 23.0 mm in length and 11.0 mm in width. Calyx shape: Cylindrical to campanulate when flower is open. Number of sepals: 5, fused to 5.0 mm to 8.0 mm below the subacute apex. Sepal dimensions: 23.0 mm in length and 8.0 mm in width. Color of sepals, outer surface: RHS 138A or RHS 138B, fading to RHS 144B at base. Color of sepals, inner surface: Ranges between RHS 145A and RHS 145B. Anthocyanin: Not present. Splitting: Yes.

*Epicalyx*.—Number of Bracts: 1 pair of 2. Bracts shape: Acuminate. Bracts dimensions: 10.0 mm in length and 13.0 mm in width. Bracts color: RHS N138A, RHS N138B, RHS N138C and RHS 144C are all present. Anthocyanin: Absent. Number of Bracteoles: 1 pair of 2. Bracteoles shape: Acute. Bracteoles dimensions: 1.0 cm in length and 0.8 cm in width. Bracteoles color: RHS N138A, RHS N138B, RHS N138C and RHS 144C are all present. Bracteoles anthocyanin: Absent.

Reproductive organs:

*Stamen number*.—10 to 20.

*Stamen dimensions*.—28.0 mm length and 0.5 mm diameter.

*Color of filaments*.—White.

*Anther number*.—20 to 40 (two per stamen).

*Anther dimensions*.—1.0 mm length and 0.5 mm in diameter.

*Color of anthers*.—White.

*Anther attachment*.—Dorsifixed.

*Pollen*.—Present.

*Style number*.—2 to 3.

*Style shoulder*.—Absent.

*Color of style*.—White.

*Style dimensions*.—20.0 mm in length and 1.0 mm in diameter.

*Stigma number*.—One on each style.

*Stigma color*.—White.

*Stigma dimensions*.—10.0 mm in length, 1.5 mm in diameter.

*Ovary position*.—Superior.

*Ovary dimensions*.—8.0 mm in length and 5.0 mm in diameter.

*Ovary shape*.—Spindle.

*Ovary color*.—Ranges between RHS 145A and RHS 145C.

Seed: Seed has been observed; color black, shape ovoid, crinkled, dimensions 0.3 cm in length and 2.0 mm in width.

I claim:

1. A new and distinct cultivar of *Dianthus* plant named 'WP11 GWE04' as described and illustrated herein.

* * * * *